United States Patent
Rohrer et al.

(10) Patent No.: US 10,852,378 B2
(45) Date of Patent: Dec. 1, 2020

(54) METHOD FOR OPTIMIZING THE PREDETERMINATION OF THE TIME PROFILE OF A CONTRAST AGENT CONCENTRATION IN DIAGNOSTIC IMAGING USING A MAGNETIC RESONANCE SYSTEM

(71) Applicant: BAYER PHARMA AKTIENGESELLSCHAFT, Berlin (DE)

(72) Inventors: Martin Rohrer, Berlin (DE); Gregor Jost, Berlin (DE); Hubertus Pietsch, Kleinmachnow (DE); Claus-Peter Reisinger, Berlin (DE); Harald Kramer, Planegg (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 476 days.

(21) Appl. No.: 15/571,353

(22) PCT Filed: May 10, 2016

(86) PCT No.: PCT/EP2016/060371
§ 371 (c)(1),
(2) Date: Nov. 2, 2017

(87) PCT Pub. No.: WO2016/180799
PCT Pub. Date: Nov. 17, 2016

(65) Prior Publication Data
US 2018/0284207 A1     Oct. 4, 2018

(30) Foreign Application Priority Data
May 13, 2015  (EP) .................................... 15167568

(51) Int. Cl.
*G01R 33/56*   (2006.01)
*A61B 5/026*   (2006.01)
(Continued)

(52) U.S. Cl.
CPC ........ *G01R 33/5601* (2013.01); *A61B 5/0263* (2013.01); *G16H 20/17* (2018.01);
(Continued)

(58) Field of Classification Search
CPC ......... A61B 6/481; A61B 6/507; A61B 5/055; A61B 5/0263; A61B 8/481
See application file for complete search history.

(56) References Cited

U.S. PATENT DOCUMENTS 5,590,654 A   1/1997  Prince
6,425,864 B1  7/2002  Foo et al.
(Continued)

FOREIGN PATENT DOCUMENTS

CN   1820710 A    8/2006
CN   103961117 A  8/2014
(Continued)

OTHER PUBLICATIONS

"A New Approach for the Estimation of MTT in Bolus Passage Perfusion Techniques" by N.A. Thacker et al. Proc. MIUA. pp. 137-140 Jul. 2000 (Year: 2000).*
(Continued)

*Primary Examiner* — Jeffrey G Hoekstra
*Assistant Examiner* — Jason M Ip
(74) *Attorney, Agent, or Firm* — James R. Stevenson; David Schramm; Joseph L. Kent (57) ABSTRACT

A method of predetermining the time profile of a contrast agent concentration at a vessel position is provided in the context of contrast agent-enhanced MRI of a region of interest only during the initial flooding-in phase of the
(Continued)

contrast agent into the vessel situated in the region of interest. The method includes establishing a broadening of a contrast agent bolus profile according to the equation $\Delta W=W2-W1$ wherein W1 is a first width of the contrast agent bolus profile at a first vessel position and W2 is a second width of a contrast agent concentration profile at a second vessel position within the region of interest. The broadening is established by determining at least one flow parameter which is dependent on at least one blood flow property of the patient at a third vessel position thereof and which correlates with the broadening of the contrast agent profile.

24 Claims, 4 Drawing Sheets

(51) Int. Cl.
    *G16H 20/17*     (2018.01)
    *G01R 33/563*     (2006.01)
    *G16H 40/60*     (2018.01)
    *A61B 5/00*     (2006.01)

(52) U.S. Cl.
    CPC ............ *G16H 40/60* (2018.01); *A61B 5/0033* (2013.01); *G01R 33/5635* (2013.01); *G01R 33/56316* (2013.01)

(56) References Cited

U.S. PATENT DOCUMENTS

| 9,743,858 | B2 | 8/2017 | Zhang et al. |
| 2003/0036694 | A1 | 2/2003 | Liu |
| 2006/0239917 | A1* | 10/2006 | Klotz ..................... A61B 6/481 424/9.3 |
| 2009/0316970 | A1 | 12/2009 | Kemper et al. |
| 2013/0044926 | A1 | 2/2013 | Kemper et al. |
| 2013/0281829 | A1 | 10/2013 | Tan et al. |
| 2014/0206991 | A1 | 7/2014 | Korporaal |
| 2014/0285194 | A1 | 9/2014 | Hutter et al. |
| 2020/0121860 | A1 | 4/2020 | Uber, III et al. |

FOREIGN PATENT DOCUMENTS

| DE | 102013204994 A1 | 9/2014 |
| JP | 2013223726 A | 10/2013 |
| JP | 2014176747 A | 9/2014 |

OTHER PUBLICATIONS

Cheong; L. et al., "An automatic approach for estimating bolus arrival time in dynamic contrast MRI using piecewise continuous regression models", Jan. 1, 2003, 48, N83-N88.
"Extended European Search Report of EP Application No. 15167568", dated Jul. 14, 2015.
Foo Thomas; et al., "Automated Detection of Bolus Arrival and Initiation of Data Acquisition in Fast, Three-dimensional, Gadolinium-enhanced MR Angiography", Jan. 1, 1997, 203, 275-280.
"Amendment in Response to the Communication Pursant to Rules 161(1) and 162 EPC in Corresponding EP Application No. 16722164. 7", dated Jul. 10, 2018.
"Communication Under Rule 71(3) EPC—Inention to Grant from corresponding EP Application No. 16722164.7", dated Oct. 26, 2018.
"International Search Report and Written Opinion from PCT Application No. PCT/EP2016/060371", dated Jul. 1, 2016.
Moran G.R.; et al., "Myocardial Viability Imaging Using Gd-DTPA: Physiological Modeling of Infarcted Myocardium, and Impact on Injection Strategy and Imaging Time", Magnetic Resonance in Medicine, 2002, 48, 791-800.
Shi; Mingguo., "Modern Medical Imaging Technology", Apr. 30, 2007, p. 199.
Strouthos; et al., "Indicator Dilution Models for the Quantification of Microvascular Blood Flow With Bolus Administration of Ultrasound Contrast Agents", IEEE, Jun. 2010, vol. 57/No. 6, 1296-1310.

* cited by examiner

METHOD FOR OPTIMIZING THE PREDETERMINATION OF THE TIME PROFILE OF A CONTRAST AGENT CONCENTRATION IN DIAGNOSTIC IMAGING USING A MAGNETIC RESONANCE SYSTEM

FIELD OF THE INVENTION

The invention relates to a method for optimizing the predetermination of the time profile of a contrast agent concentration at a vessel position in a region of interest in the case of a contrast agent-enhanced Magnetic Resonance (MR) imaging of a patient only during the first flooding-in phase of the contrast agent.

BACKGROUND OF THE INVENTION

Magnetic resonance imaging (MRI) methods are well known in diagnostic imaging. A contrast agent is often employed for accentuating the vascular system in relation to the remaining tissue, particularly for displaying blood vessels in magnetic resonance angiography (MRA). Such methods are referred to as contrast-enhanced MR angiography (CE-MRA). If MRI scans are made of peripheral blood vessels, e.g., leg arteries, this is referred to as contrast-enhanced peripheral MR angiography (CE-pMRA).

Compared to other imaging techniques not enhanced by contrast agents, CE-MRA constitutes the preferred technique for radiation-free, non-invasive vessel diagnostics in many clinical cases. It was performed for the first time about 20 years ago, the technique was improved continuously since then and these days it constitutes an advanced diagnostic standard method in most countries.

In most cases, the clinical questions require a visualization of the arterial vessel system that has the highest possible contrast in relation to the surrounding tissue, with the simultaneous visualization of the venous vessel system being generally considered to be an interfering superposition. Therefore, the method according to the invention described here also only relates to contrast-enhanced MR examinations in which only the first flooding-in phase of the contrast agent is used for imaging, i.e., so-called "first-pass" MR examinations, and it is essential to avoid venous superpositions by way of technical measures and optimizations, or to keep these slight as possible.

In principle, what is important to this end is a synchronization, to second accuracy where possible, of the contrast agent flooding into the vessel system of the target region with the start of the data acquisition, in order both to fully be able to use the available contrast enhancement by the contrast agent and also to stay ahead of the subsequent return flood of the contrast agent in the venous vessel system. Thus, in contrast to the application of contrast agents in computed tomography (CT) or CT angiography, in which the blood vessels of a region to be examined are flooded with contrast agent in the typical range of approximately 25-50 seconds, the contrast agent is applied over a substantially shorter time period within the typical range of approximately 3 to 15 seconds.

Moreover, compared to contrast agent-enhanced fluoroscopic x-ray or CT examinations, what should be mentioned is that, in the contrast agent-enhanced MR examination, smaller volumes are considered, an acquisition technique which is different as a matter of principle and has peculiarities in the k-space acquisition and Fourier transformation, different measurement times and requirements on the contrast agent concentration during the measurement and a nonlinear signal intensity as a function of the local contrast agent concentration in the examination region are present. Thus, direct transfer of the conditions in CT during contrast agent application to those in MRI is generally not possible.

A plurality of different processes are known for synchronizing an applied contrast agent bolus in CE-MRA (bolus timing).

(i) Use of a test bolus for prospective determination of the expected duration required by the injected contrast agent bolus to travel from the site of the intravenous injection to the target region in the body (bolus travel time=BTT, bolus arrival time=BAT, region of interest=ROI).

Here, the BTT is measured by means of a test bolus prior to the actual CE-MRA. Here, the test bolus is typically approximately 10%-15% of the actual contrast agent volume. The examination usually contains a preceding procedure, which consists of the time-resolved 2D measurement of a previously carefully set acquisition window in the target region. Here, the signal intensity (SI) affected by the intravenously injected test bolus is measured quantitatively within a large artery, usually below the aorta bifurcation (e.g., A. iliaca, A. poplitea). The SI is measured as a function of the time with a time resolution of typically 1 second from the time of the test bolus injection. In principle, the start of an injection counts as the start time. In general, the test bolus injection is brought about with the same injection rate also provided for the actual contrast agent injection (e.g., 1 ml/s), followed by a saline injection. The BTT and also the broadening of a bolus in the target region can be gathered from the measured flooding-in curve of the test bolus in the selected body region.

Such a method is largely robust and well established. In the case of the correct application by experienced staff, it leads to good results in most cases. However, the method is time-consuming since a number of minutes are lost in the test bolus measurement and evaluation thereof.

In at least a small (single digit) percentage of total applications, even experienced users report problems in respect of the fact that the correct test bolus detection is very difficult or impossible. The reasons for this are not uniquely known. Possible reasons are bolus dispersion that is too strong and a thinning effect that is too strong due to specific cardiovascular conditions. Further disadvantages of this method include the additional contrast agent use, or a dose that is too low during the actual contrast agent examination to compensate for the previously applied test bolus. Moreover, the test bolus applied prior to the examination can lead to unwanted background effects since contrast agent from the test bolus is already situated in the interstitium during the actual examination.

(ii) "Fluoroscopic" methods for directly determining the contrast agent flooding-in the ROI, without previously measuring the BTT.

Like in the dynamic measurement of the test bolus according to (a) above, a suitably selected two-dimensional image representation can also be used to observe flooding-in of the actual contrast agent bolus in real-time, immediately before reaching the target region. What is important here is that a suitable region is observed at a time resolution in the region of at least one second just upstream of the actual ROI in terms of flow such that the flooding-in is identified reliably and in time. As soon as there is detection of the bolus flooding-in, the measuring program must be switched within a very short period of time from time-resolved two-dimensional acquisition to the desired, generally three-dimensional acquisition with a high spatial resolution. To this end, different, partly manufacturer-specific and automated methods of data acquisition are known.

It is advantageous here that it is possible to make do without loss of time and contrast agent as there is no need for a test bolus measurement. However, what is disadvantageous is that, in principle, a remaining inaccuracy of the actual BAT in the target region remains because the contrast agent flooding-in always needs to be observed just above the target region in order still to ensure the technically required period of time of a few seconds for switching from the time-resolved 2D bolus detection to the 3D acquisition of the ROI with a high spatial resolution. This remaining, unknown period of time must be replaced by empirical values and rules of thumb which, due to the partly very strong, individual physiology and cardiovascular pathologies, leads at least in individual cases to a deterioration of the results.

(iii) "4D" data acquisition without previous determination of the bolus arrival time and without specific triggering of the measurement by the contrast agent bolus.

In this method, a compromise between spatial and time resolution of the obtained image data is accepted as a matter of principle by virtue of the contrast agent flooding-in being achieved with a dynamically repeated acquisition of the three-dimensional target region, for example in each case within 3 to 5 seconds. However, in these short measurement times, the spatial resolution is limited and typically at least 2 mm-3 mm. In the case of a 3D acquisition with a high spatial resolution, e.g., 1 mm in all spatial directions or better, the measurement time is usually around 15 seconds. As a result of the dynamically repeated measurements, the contrast agent bolus is certainly recorded, usually even in a plurality of 3D data records. Therefore, bolus synchronization is superfluous. In this method, the additionally obtained dynamic information of the contrast agent flooding-in is advantageous, but the worse spatial resolution is disadvantageous.

Despite significant technical progress in recent years, the ideal time synchronization of the contrast agent bolus in the target region (bolus timing) and the ideal use of the injected contrast agent bolus often remains a challenge for the staff since much experience and basic physical understanding of the technically complicated MRI method are required.

Particularly peripheral angiography, which is important in vessel diagnostics, for identifying vessel disease caused by diabetes, such as, e.g., peripheral arterial occlusive disease, cardiovascular diseases or "smoker's leg", of the lower limbs is still connected with an unwanted high rate of artefact-affected and non-diagnostic examination results.

Overall, there is the need to be able to predict as accurately as possible the contrast agent concentration profile with time after administering a bolus at one point in the vessel system of a patient, wherein, however, the use of a test bolus applied prior to the examination is intended to be dispensed with.

It is therefore an object of the invention to enable the prediction of the broadening of a bolus for the purposes of improving the method for determining the contrast agent profile at a predetermined position in the blood circulation during diagnostic imaging with a magnetic resonance system in the blood circulation of the patient, wherein the administration of a test bolus in the examined patient is dispensed with.

This object is achieved by the features of the independent patent claims. Advantageous developments of the invention are the subject matter of dependent claims.

SUMMARY

The inventors have recognized that, in contrast to the relatively long, in terms of time, contrast agent administrations during a CT examination, where a small broadening (dispersion) of the bolus in relation to the duration of the flooding-in barely plays a role, it is necessary in contrast agent-enhanced MR imaging, in particular of arterial blood vessels, to know and to take into account the effect of the broadening of a short contrast agent administration, in particular within the region of a few seconds, in order to be able to predict the contrast agent profile as exactly as possible. Furthermore, the inventors have identified that there is an evaluable correlation between the variable of broadening and the blood flow properties, such as, e.g., the flow velocity or the volume flow, of the blood in the vessel system at the selected location or of the velocity difference between two selected locations, which correlation makes it possible to predict an occurring broadening of a contrast agent bolus. In order to obtain correlation values which are as meaningful as possible, it is particularly advantageous here if, where possible, comparable patient constitutions are also used when establishing the correlation values, i.e., if use is made of parameters such as sex, height, weight, etc. that are fit to the patient to be examined.

Since it is possible to determine the flow velocity or the blood flow and other blood flow properties correlated therewith at predetermined locations in the vessel system without applying a contrast agent by means of a phase contrast magnetic resonance measurement, it now becomes possible to deduce the broadening of the contrast agent bolus to be expected at predetermined vessel positions with the aid of a determination of the blood flow properties without contrast agent, which is carried out directly before the examination.

Therefore, it is possible to determine the correlation between the broadening of an applied contrast agent bolus and blood flow properties measured in the vessel system, or parameters derived therefrom, by means of preceding, possibly contrast agent-enhanced examinations on comparable patient collectives. In the case of the contrast agent-enhanced examination of a patient, it is initially possible to determine the corresponding blood flow property or parameters dependent thereon, without contrast agent being present, and, from this, deduce the expected broadening of the bolus, for example by using a lookup table (LUT). Since it is known that the travel time of a bolus is also dependent on the flow velocities or volume flows present, such an LUT can also be generated for determining the travel time of the bolus (BTT), or a different known process can be used here for predicting a BTT. Using both items of information it is then possible to predict the actual expected start and end time of an applied bolus and use this for time synchronization of an applied bolus with a contrast agent-enhanced MRI measurement.

All information required for this can be established in a current examination of a patient with the aid of a phase contrast MRI examination without the presence of a contrast agent. Since no other previously applied contrast agent, which can lead to an increased background noise, i.e. to a worse signal-to-noise ratio, and therefore to worse image results, is present in the body of the patient during the measurement, this moreover results in an improvement in the image quality. This applies in particular because the method according to the invention only relates to MR examinations in which the MR examination is undertaken in the "first pass", i.e. in the first flooding-in phase of the applied contrast agent in the region of the observed ROI, and therefore there is no contrast agent in the "background" during imaging.

The above-described method is particularly suitable for representation in the periphery of the lower extremities (CE-pMRA) since the current limitations in the prior art are regularly based on inaccurate or incomplete knowledge of the user regarding individual cardiovascular conditions in the patient, as are present immediately prior to the contrast agent examination. As a result of the flow velocities being determined immediately before the imaging contrast agent examination, there is particularly current, more accurate and more comprehensive knowledge about the individual cardiovascular conditions of the patient than was previously conventional as the current stress levels of the patient in the region of interest are automatically also considered.

The previously practised method, based on accurate knowledge of a single individual scalar parameter, such as the bolus arrival time (BAT) in seconds after the start time of the contrast agent injection or the bolus transfer time (BTT), is a necessary but not a sufficient condition for the diagnostically optimized CE-pMRA in all examination cases. The contrast agent concentration profile to be expected can now be understood and determined more accurately due to the additional prediction and knowledge of the broadening of the contrast agent bolus on the path thereof from the site of the injection to the target region (ROI).

Thus, according to the invention, it is possible to perform blood flow measurements at different positions of the arterial vessel system in order to obtain knowledge about the acute and patient-specific cardiovascular conditions on the basis of a postulated and, for the first time, verified correlation between the bolus dispersion and various blood flow parameters such that a necessary contrast agent bolus for achieving a desired contrast agent concentration profile and the timing relative to carrying out the MR examination can be correctly selected with improved reliability.

Accordingly, the inventors propose a method for optimizing the predetermination of the time profile of a contrast agent concentration at a vessel position in a region of interest in the case of a contrast agent-enhanced MR image of a patient only during the first flooding-in phase (first pass) of the contrast agent, in which a broadening of a contrast agent bolus profile with a first width at a predetermined first vessel position of a patient in relation to a contrast agent concentration profile with a second width at a predetermined second vessel position, which is arranged in the region of interest, is established by determining at least one flow parameter which is dependent on at least one blood flow property at a third vessel position and which correlates with the broadening.

Reference is made to the fact that the term contrast agent concentration profile should not only be understood to mean the profile of the actual concentration of the contrast agent in the blood, but also the profile of the contrast agent-caused increase of the MR signal during an MR examination. Furthermore, the method is specifically provided to determine the contrast agent bolus profile for vessel positions which are arranged downstream of the cardiopulmonary passage in relation to the flow, i.e., arranged behind the heart in arterial terms; in particular, this should be understood to mean peripheral vessel positions and/or regions of interest which are situated in a peripheral region of the patient, in particular in one of the limbs.

Therefore, the established broadening to be expected for predetermining the contrast agent concentration profile over time at a predetermined vessel position can be made available for further use; storage is preferably carried out in an electronic memory for further use by computer.

In particular, the at least one blood flow property can be established without the presence of contrast agent by way of a phase contrast magnetic resonance measurement. Such a measurement can be undertaken immediately before the actual MR examination such that, advantageously, such a measurement takes into account the currently actually present constitution and state of the examined patient and is therefore ideally tuned to the actual MR examination.

In principle, it is possible to combine determining the broadening of a bolus according to the invention with determining a bolus transfer time BTT or a bolus arrival time BAT, which optionally also uses a test bolus, as known in the prior art in order overall to predict a contrast agent concentration profile. However, it is particularly advantageous if the additionally determined bolus transfer time between the first vessel position and the second vessel position or the bolus arrival time is also determined on the basis of a predetermined correlation with a blood flow property measured without contrast agent.

What is further proposed for the purposes of optimizing the predetermination of the time profile of a contrast agent concentration at a vessel position in a region of interest in the case of a contrast agent-enhanced MR imaging of a patient is to carry out the following method steps:

establishing a correlation between a broadening of at least one contrast agent bolus profile present at the first vessel position with a first width in relation to the contrast agent concentration profile with a second width at the second vessel position using a flow parameter dependent on at least a blood flow property at a third vessel position, taking into account at least one patient parameter of an examined patient collective, determining at least one current flow parameter of the patient, selecting a desired contrast agent concentration profile at the second vessel position and establishing the contrast agent bolus profile required therefor from the previously established correlation, taking into account at least one patient parameter of the patient, selecting the necessary contrast agent bolus profile at a contrast agent injection device or transmitting the necessary contrast agent bolus profile to a contrast agent injection device for use in a contrast agent-enhanced MR examination, in particular an MR angiography.

What is also proposed according to the invention is that determining the blood flow property at least at the third vessel position of the patient is performed by a phase contrast magnetic resonance examination. In particular, the phase contrast magnetic resonance examination for determining the blood flow property can be performed here without contrast agent being present in the blood circulation of the patient.

So that, where possible, a data pool of preliminary examinations, in which the broadening established there is as characteristic as possible of the current patient, is also resorted to for the current patient to be examined. The patient collective, from which the data of the preliminary examinations in respect of the broadening originate, should be as similar as possible to the currently examined patient. This can be ensured by virtue of the fact that the current patient and the relevant patient collective, from which the data of the preliminary examinations in relation to the broadening originate, correspond in terms of as many patient parameters as possible. In particular, patient parameters which have anatomical, physiological and medical relevance to the circulation and to the vessel structure should be considered here. In particular, according to this, at least one of the following variables can be used as at least one patient parameter: sex, weight, height, age, heart rate and/or body mass index (BMI).

Moreover, reference is also made to the fact that, in addition to the aforementioned patient parameters, the contrast agent itself can be introduced as an additional parameter characterizing the broadening. Accordingly, the proposed LUT can be extended by this contrast agent parameter for typifying the contrast agent employed, without departing from the scope of the invention.

In respect of the considered blood flow properties, very different flow properties which have a correlation with the broadening of a bolus can be used. What should be noted here is that—as is well known—the blood flow through a vessel generally cannot be defined by a single directly measurable variable which is constant over the vessel cross section and over the pulse phase and for a relatively long period of time. Thus, the blood flow through a vessel at a vessel position is not only characterized by a speed in cm/s or a blood flow in ml/s but also by profiles that change in time and space. Nevertheless—or precisely because of this—it is possible by way of appropriate measurements to express characteristic properties of the blood flow, such as, e.g., minimum, maximum or average values of speed and flow, which have a good correlation with the broadening of a bolus.

Accordingly, to this end, the inventors propose that at least one of the following properties—wherein each individual item in the list itself again contains a plurality of properties which are in turn usable on their own—is used as at least one blood flow property:

maximum, minimum or mean blood flow velocity at at least one predetermined position in the vessel cross section at the vessel position;
maximum, minimum or mean blood flow velocity at at least one predetermined position in the vessel cross section at the vessel position at a given heart or pulse phase;
maximum, minimum or mean blood flow velocity at at least one predetermined position in the vessel cross section at the vessel position at a given heart or pulse phase over a predetermined measurement time period;
maximum, minimum or mean blood flow volume at at least one predetermined position in the vessel cross section at the vessel position;
maximum, minimum or mean blood flow volume at at least one predetermined position in the vessel cross section at the vessel position at a given heart or pulse phase;
maximum, minimum or mean blood flow volume at at least one predetermined position in the vessel cross section at the vessel position at a given heart or pulse phase over a predetermined measurement time period;
a geometric property of a velocity profile over the vessel cross section at the vessel position;
net forward volume over a predetermined period of time or per heartbeat.

In a particularly simple embodiment variant of the method according to the invention, the blood flow property itself can be used as flow parameter.

In principle, it is also not only possible to perform the measurement of the blood flow properties at one vessel position, but also to establish these properties at different vessel positions and thereby also obtain a particularly strong statement about the properties of the path between the vessel points and therefore about vessel properties, which statement is particularly correlated with the broadening of a bolus over a vessel path.

Accordingly, it is proposed likewise to measure blood flow properties at at least one fourth vessel position and to use an absolute or percentage difference between the blood flow property at the third vessel position in relation to preferably the same blood flow property at the at least one fourth vessel position as flow parameter.

In respect of particularly advantageous vessel positions for the measurement to be carried out, the inventors make the following suggestions.

Accordingly, the first vessel position can satisfy at least one of the following locations or conditions:
the first vessel position lies in a venous vessel,
the first vessel position lies in an arm vein,
the first vessel position lies on the back of the hand,
the first vessel position lies at a central venous catheter,
the first vessel position lies between the back of the hand and the Vena axillari,
the first vessel position lies between the foot and the Vena saphena magna,
the first vessel position lies in a central venous vessel.

The second vessel position should satisfy at least one of the following locations or conditions:
the second vessel position lies in an arterial vessel,
the second vessel position lies in a leg artery,
the second vessel position lies downstream of the third vessel position,
the second vessel position lies downstream of the bifurcation,
the second vessel position lies in a peripheral artery, preferably in the knee region,
the second vessel position lies in the arm region,
the second vessel position lies in the neck region.

In respect of the third vessel position, what is proposed is that the third vessel position satisfies at least one of the following locations or conditions:
the third vessel position is the second vessel position,
the third vessel position lies in the Aorta thorakalis,
the third vessel position lies in the Aorta abdominalis,
the third vessel position lies between the Aorta thorakalis,
the third vessel position lies upstream of the bifurcation,
the third vessel position lies between the bifurcation and the second vessel position.

If a measurement at a fourth vessel position is used, the inventors propose that the fourth vessel position should satisfy at least one of the following locations or conditions:
the fourth vessel position lies upstream of the third vessel position,
the fourth vessel position lies downstream between the third vessel position and the second vessel position,
the fourth vessel position lies downstream of the second vessel position.

The method according to the invention only relates to contrast agent-enhanced MR examinations and does not relate to CT examinations. As presented previously, a peculiarity that emerges from this is that the time period of a bolus administration must be particularly short. Therefore, in relation to the width of the contrast agent bolus profile, the inventors propose that the former lies in the range of 1 to 20 seconds, preferably 3 to 15 seconds. Naturally, taking into account that respectively present broadening, the width of the contrast agent concentration profile in the vessel system is within a similar time frame. While the width of the contrast agent bolus profile is uniquely determined due to the steep edges thereof, there is a certain amount of fuzziness in the definition of the width of the contrast agent concentration profile. Therefore, a person skilled in the art will generally set the width to be the full width at half maximum of the contrast agent concentration or of a signal generated by the contrast agent or use the attainment of a predetermined signal value or the attainment of a signal level generated thereby to define the width. However, the same definition of width should be used in each case in order to obtain comparable statements between the data from the preliminary examinations and the current measurement data in an MR examination of the patient.

In principle a previously established correlation between the expected broadening and the respectively considered flow parameter can be represented as desired within the scope of the invention, for example also by using a mathematically described functional relationship. However, the application of a "lookup" table (LUT) is particularly advantageous and simple such that the correlation of the broadening with the flow parameter is gathered from a preferably electronically stored table. Here, the table predetermined from reference measurements can also contain at least one of the aforementioned patient parameters. Alternatively, the correlation of the broadening with the flow parameter can be calculated by a function predetermined from reference measurements, wherein also the function predetermined from reference measurements can also contain at least one patient parameter as a variable.

In addition to the above-described method, the scope of the invention also includes a computer, at least comprising a memory for programs, which are executed during operation, wherein programs which execute the method according to the invention in accordance with a feature combination disclosed herein are stored there.

Furthermore, the scope of the invention also includes a magnetic resonance system for generating a contrast agent-enhanced MR image or an MR vessel depiction comprising a contrast agent injector controlled by a computer, the computer being equipped with a memory for programs which are executed during operation, wherein programs which execute the method according to the invention are stored.

In a related aspect, the invention provides a method of predetermining a time profile of contrast agent concentration at a position in a blood vessel of a patient in the context of contrast agent-enhanced magnetic resonance (MR) imaging of a region of interest only during an initial flooding-in phase of the contrast agent into the blood vessel situated in the region of interest. The method includes establishing an expected broadening of a contrast agent bolus profile B(t) according to the equation $\Delta W=W2-W1$ wherein W1 is a first width of the contrast agent bolus profile B(t) at a predetermined first vessel position of the patient and W2 is a second width of a contrast agent concentration profile K(t) at a predetermined second vessel position situated in the region of interest of the patient. The expected broadening is established by determining at least one flow parameter which is dependent on at least one blood flow property of the patient at a third vessel position thereof and which correlates with the expected broadening of the contrast agent bolus profile B(t).

In certain non-limiting embodiments of the aforementioned method, the region of interest and/or the predetermined second vessel position therein is situated downstream of a cardiopulmonary passage of the patient in relation to flow of blood therein. The region of interest and/or the predetermined second vessel position is situated in a peripheral region of the patient such as in one of the limbs. The expected broadening may be stored in an electronic memory for further use by a computer. The at least one blood flow property may be established without the presence of contrast agent by way of a phase contrast magnetic resonance measurement. The method can also be used to determine a bolus transfer time and/or a bolus arrival time between the predetermined first vessel position and the predetermined second vessel position. The contrast agent concentration profile (K(t)) at the second vessel position may be determined from the expected broadening and either the bolus transfer time or the bolus arrival time or both.

In another aspect, the invention provides a method of predetermining a time profile of contrast agent concentration at a position in a blood vessel in a region of interest of a patient (P) in connection with a contrast agent-enhanced magnetic resonance (MR) imaging procedure to be performed on the patient. The method includes establishing a correlation between a broadening ($\Delta W=W2-W1$) of at least one contrast agent bolus profile (B(t)) having a first width (W1) at a first vessel position (P1) in relation to a contrast agent concentration profile (K(t)) having a second width (W2) at a second vessel position (P2), the correlation being established using a flow parameter ($P_G$) dependent upon at least a blood flow property ($f_B$) of the patient (P) at a third vessel position (P3) thereof and taking into account at least one patient parameter ($P_P$) of an examined patient collective. The method further includes determining from the patient (P) at least one flow parameter ($P_{Pa}$) currently representative thereof; selecting a desired contrast agent concentration profile (K(t)) to be achieved at the second vessel position (P2) and, using the correlation, determining a necessary contrast agent bolus profile (B(t)) required therefor, taking into account at least one patient parameter ($P_P$) of the patient (P); and enabling the necessary contrast agent bolus profile (B(t)) to be one of selectable from or transmittable to an injection device for use in a contrast agent-enhanced MR examination such as MR angiography.

In certain non-limiting embodiments of the aforementioned method, the blood flow property ($f_B$) of the patient at the third vessel position (P3) is determined via a phase contrast magnetic resonance examination. The phase contrast magnetic resonance examination for determining the blood flow property ($f_B$) may be performed without the contrast agent being present in a blood circulation of the patient (P). At least one of the following variables may be used as the at least one patient parameter ($P_P$): sex, weight, height, age, heart rate, body mass index, type of stature, and distance between the vessel positions.

In certain non-limiting embodiments of the aforementioned method, at least one of the following properties may be used as the blood flow property ($f_B$): (a) maximum, minimum or mean blood flow velocity ($v_G$) at at least one predetermined position in a cross section of the blood vessel at the vessel position; (b) maximum, minimum or mean blood flow velocity ($v_G$) at at least one predetermined position in a cross section of the blood vessel at the vessel position at a given heart or pulse phase; (c) maximum, minimum or mean blood flow velocity ($v_G$) at at least one predetermined position in a cross section of the blood vessel at the vessel position at a given heart or pulse phase over a predetermined measurement time period; (d) maximum, minimum or mean blood flow volume at at least one predetermined position in a cross section of the blood vessel at the vessel position; (e) maximum, minimum or mean blood flow volume at at least one predetermined position in a cross section of the blood vessel at the vessel position at a given heart or pulse phase; (f) maximum, minimum or mean blood flow volume at at least one predetermined position in a cross section of the blood vessel at the vessel position at a given heart or pulse phase over a predetermined measurement time period; (g) a geometric property of a velocity profile over a cross section of the blood vessel at the vessel position; and (h) net forward volume over a predetermined period of time or per heartbeat.

In certain non-limiting embodiments of the aforementioned method, the blood flow property ($f_B$) itself may be used as the flow parameter ($P_G$). The flow parameter ($P_G$) may also be an absolute or percentage difference between the blood flow property ($f_B$) at the third vessel position (P3) in relation to the blood flow property ($f_B$) of a same type at a fourth vessel position (P4).

In certain non-limiting embodiments of the aforementioned method, the first vessel position (P1) satisfies at least one of the following locations or conditions: (a) the first vessel position (P1) lies in a venous vessel; (b) the first vessel position (P1) lies in an arm vein; (c) the first vessel position (P1) lies on the back of the hand; (d) the first vessel position (P1) lies at a central venous catheter; (e) the first vessel position (P1) lies between the back of the hand and the V. axillari; (f) the first vessel position (P1) lies between a foot and the V. saphena magna; and (g) the first vessel position (P1) lies in a central venous vessel. The second vessel position (P2) satisfies at least one of the following locations or conditions: (a) the second vessel position (P2) lies in an arterial vessel; (b) the second vessel position (P2) lies in a leg artery; (c) the second vessel position (P2) lies downstream of the third vessel position (P3); (d) the second vessel position (P2) lies downstream of the bifurcation of the aorta; (e) the second vessel position (P2) lies in a peripheral artery in a knee region; (f) the second vessel position (P2) lies in an arm region; and (g) the second vessel position (P2) lies in a neck region. The third vessel position (P3) satisfies at least one of the following locations or conditions: (a) the third vessel position (P3) is the second vessel position (P2); (b) the third vessel position (P3) lies in the Aorta thorakalis; (c) the third vessel position (P3) lies in the Aorta abdominalis; (d) the third vessel position (P3) lies between the Aorta thorakalis and (P2); (e) the third vessel position (P3) lies upstream of the bifurcation of the aorta; and (f) the third vessel position (P3) lies between the bifurcation and second vessel position (P2). The fourth vessel position (P4) satisfies at least one of the following locations or conditions: (a) the fourth vessel position (P4) lies upstream of the third vessel position (P3); (b) the fourth vessel position (P4) lies downstream between the third vessel position (P3) and the second vessel position (P2); and (c) the fourth vessel position (P4) lies downstream of the second vessel position (P2).

In certain non-limiting embodiments of the aforementioned method, a width of the contrast agent bolus profile (B(t)) lies in the range of 3 to 15 seconds preferably but not outside of the range of 1 to 20 seconds. The correlation between the broadening ($\Delta W = W2 - W1$) and the flow parameter ($P_G$) may be gathered from a stored lookup table. The stored lookup table is predetermined from reference measurements and contains at least one of the following parameters as the at least one patient parameter ($P_P$): sex, weight, height, age, heart rate, body mass index, type of stature, and distance between the vessel positions. Alternatively, the correlation between the broadening ($\Delta W = W2 - W1$) and the flow parameter ($P_G$) may be calculated by a function (f($P_G$, $P_P$)) predetermined from reference measurements. The function (f($P_G$, $P_P$)) may also contain at least one of the following parameters as the at least one patient parameter ($P_P$): sex, weight, height, age, heart rate, body mass index, type of stature, and distance between the vessel positions.

In another aspect, the invention provides a magnetic resonance system that includes a contrast agent injector controlled by a computer. The computer is preferably equipped with a memory for storing a program therein. The program comprises at least in part a method of predetermining a time profile of contrast agent concentration at a position in a blood vessel of a patient in the context of contrast agent-enhanced magnetic resonance imaging of a region of interest only during an initial flooding-in phase of the contrast agent into the blood vessel situated in the region of interest. The method, when executed by the computer, is capable of at least establishing an expected broadening of a contrast agent bolus profile B(t) according to the equation $\Delta W = W2 - W1$ wherein W1 is a first width of the contrast agent bolus profile B(t) at a predetermined first vessel position of the patient and W2 is a second width of a contrast agent concentration profile K(t) at a predetermined second vessel position situated in the region of interest of the patient. The expected broadening may be established by determining at least one flow parameter which is dependent on at least one blood flow property of the patient at a third vessel position thereof and which correlates with the expected broadening of the contrast agent bolus profile B(t).

Moreover, it also lies within the scope of the invention if, instead of, or in addition to, determining the bolus broadening, a correlation between the bolus transfer time and at least one of the flow parameters described herein is established empirically, and possibly in a patient parameter-dependent manner, in the same manner and stored correspondingly such that, for the current examination of a patient, also the BTT, by an immediately preceding contrast agent-free phase contrast MR examination, at least one required flow parameter is determined and the bolus transfer time to be expected is predicted on the basis of the established correlation.

DETAILED DESCRIPTION OF THE DRAWINGS

Subsequently, the invention is described in more detail on the basis of the figures, wherein only features required for the understanding of the invention are depicted. In detail.

DETAILED DESCRIPTION OF THE INVENTION

Figure 1:
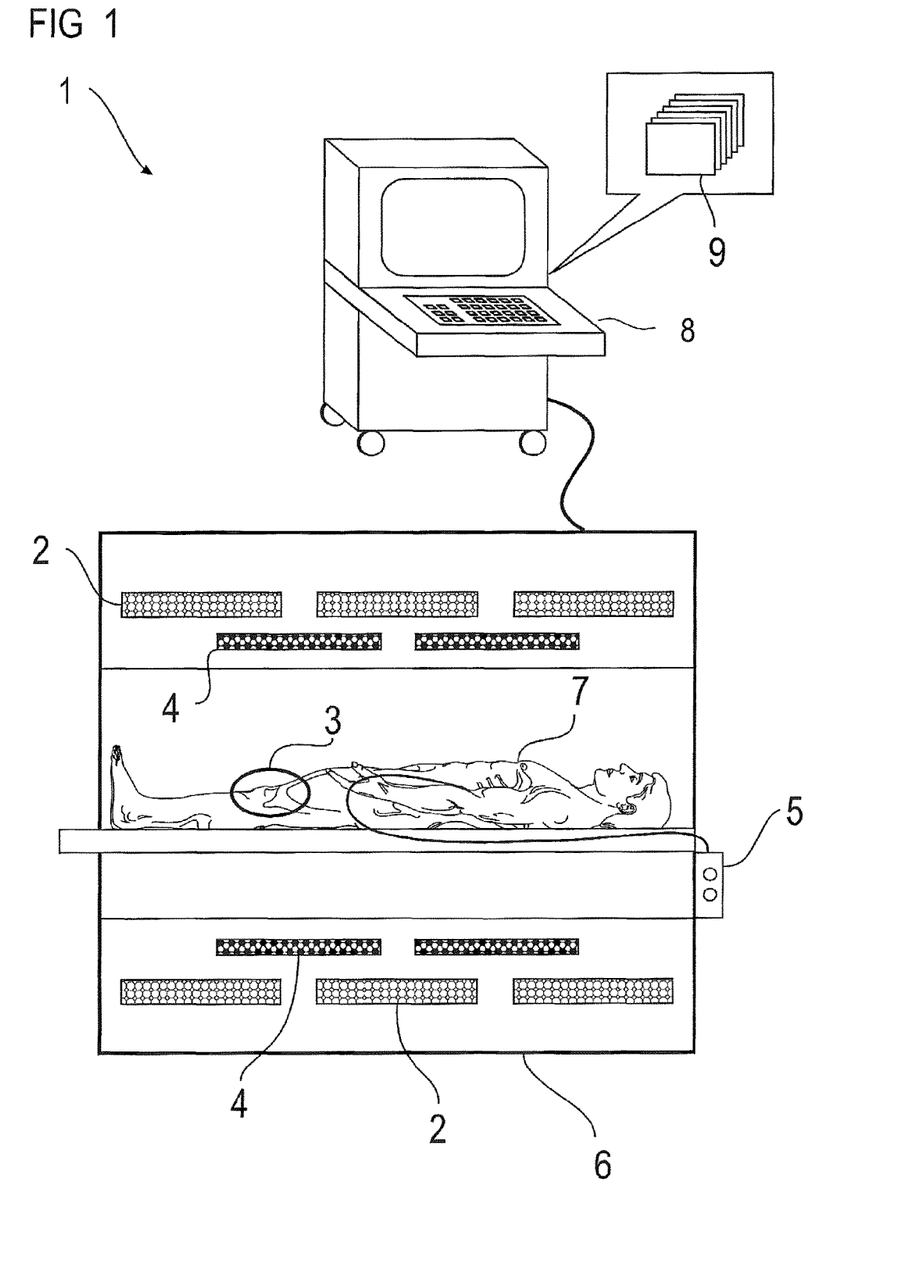
FIG. 1 shows an illustration of an MRI system according to the invention.

FIG. 1 schematically depicts a magnetic resonance imaging system (MRI system) 1. In this MRI system 1, magnetic coils 2 for generating a strong main magnetic field are situated in a housing 6. As a result of the magnetic field, the hydrogen nuclei in the body of the patient 7, in accordance with the spin thereof, are aligned parallel or antiparallel to the magnetic field lines. By exciting the atomic nuclei with an alternating electromagnetic field at the resonance frequency, the atomic nuclei resonate. After switching off the excitation frequency, the atomic nuclei return to their unexcited state and emit energy in the form of electromagnetic radiation energy, which is measured with the aid of reception coils 3, which are arranged, where possible, in the vicinity of the ROI to be observed on the patient 7. Additional magnetic fields with defined field gradients are generated by additional magnet coils 4, as a result of which the signals emitted by the nuclei contain spatial information, by means of which the position of the emitted signal is definable. The control and computer unit 8 controls this system 1, evaluates the measurement signals and, in the memory thereof, has programs 9 which, in addition to control and image calculation, also carry out the method according to the invention.

For an improved depiction of blood vessels, it is sometimes necessary to briefly enrich the blood circulation of the patient with contrast agent, for the purposes of which use is usually made of a contrast agent injector 5 which, under electronic control—either by the computer unit 8 or by a different, separate computer unit—generates the volume flow of a contrast agent to be applied for the measurement.

With the aid of such an MRI system, it is possible, even when using a plurality of reception antennas, to obtain blood flow information, such as, e.g., flow velocities, velocity profiles or volume flows, without the application of a contrast agent. In this respect, reference is made, merely by way of example, to U.S. Patent Application Publication 2014/0285194A1 and German Patent Application Publication DE 102013204994 A1 corresponding thereto.

Figure 2:
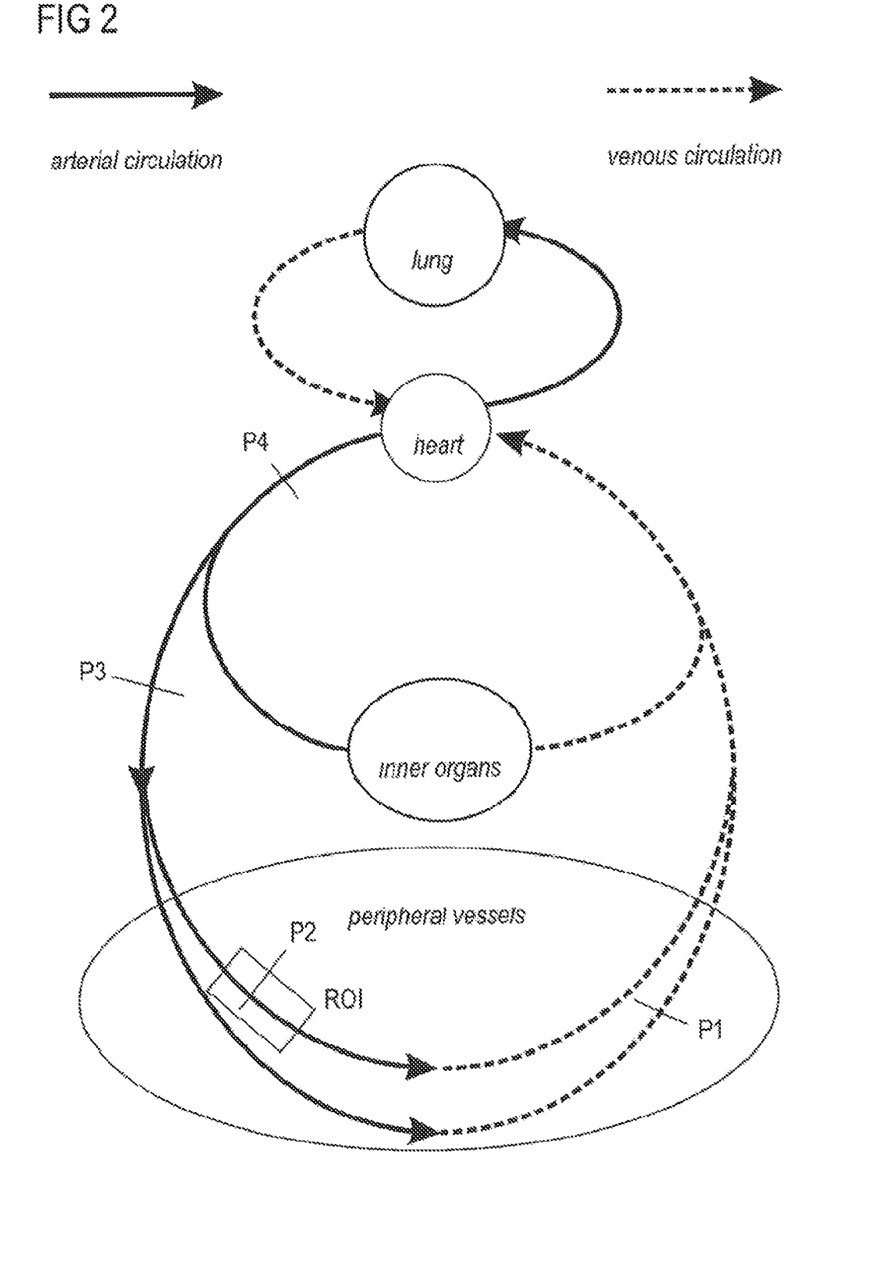
FIG. 2 shows an illustration of the circulation of a patient.

For an improved understanding of the invention, FIG. 2 shows a schematic depiction of the blood circulation of a patient. This closed circulation is divided into a venous circulation (dashed lines) and an arterial circulation (full lines) and is substantially operated by the pumping action of the heart. In the pulmonary circulation—in contrast to the remaining circulation—the arterial blood has a low oxygen content and the venous blood has a high oxygen content. In accordance with such a natural profile and the relatively easily producible and usable accesses in the venous zone, for example at an arm or hand vein, contrast agents are usually applied through such accesses, usually with the aid of automatically controlled contrast agent injectors. Accordingly, a bolus placed there initially passes the right cardiac chambers (not depicted in any more detail), is guided by the pulmonary passage to the left chambers of the heart (likewise not depicted here) and from there it reaches the regions of the body which are intended to be depicted with an MR image and which are of interest in relation to the invention; in particular, it also reaches the peripheral vessel regions.

In the schematic illustration of FIG. 2, the essential vessel positions P1 to P4 and the region of interest ROI to be imaged are marked at exemplary and typical positions. As mentioned previously, the application usually occurs in the zone of the venous circulation, corresponding to the plotted vessel position P1 at a peripheral vessel, e.g. of an arm or hand vein. The region of interest ROI, which is to be examined by imaging, can—as plotted here—for example lie in the region of a leg artery, in which the vessel position P2 is then also situated. The further measurement positions, at which blood flow properties are then determined, then generally lie in the arterial vessel system between the left atrium of the heart and the ROI. However, reference is made to the fact that positioning of the measurement points at vessel positions which, as seen in the flow direction, are arranged downstream of the ROI or P2 is also possible.

Figure 3:
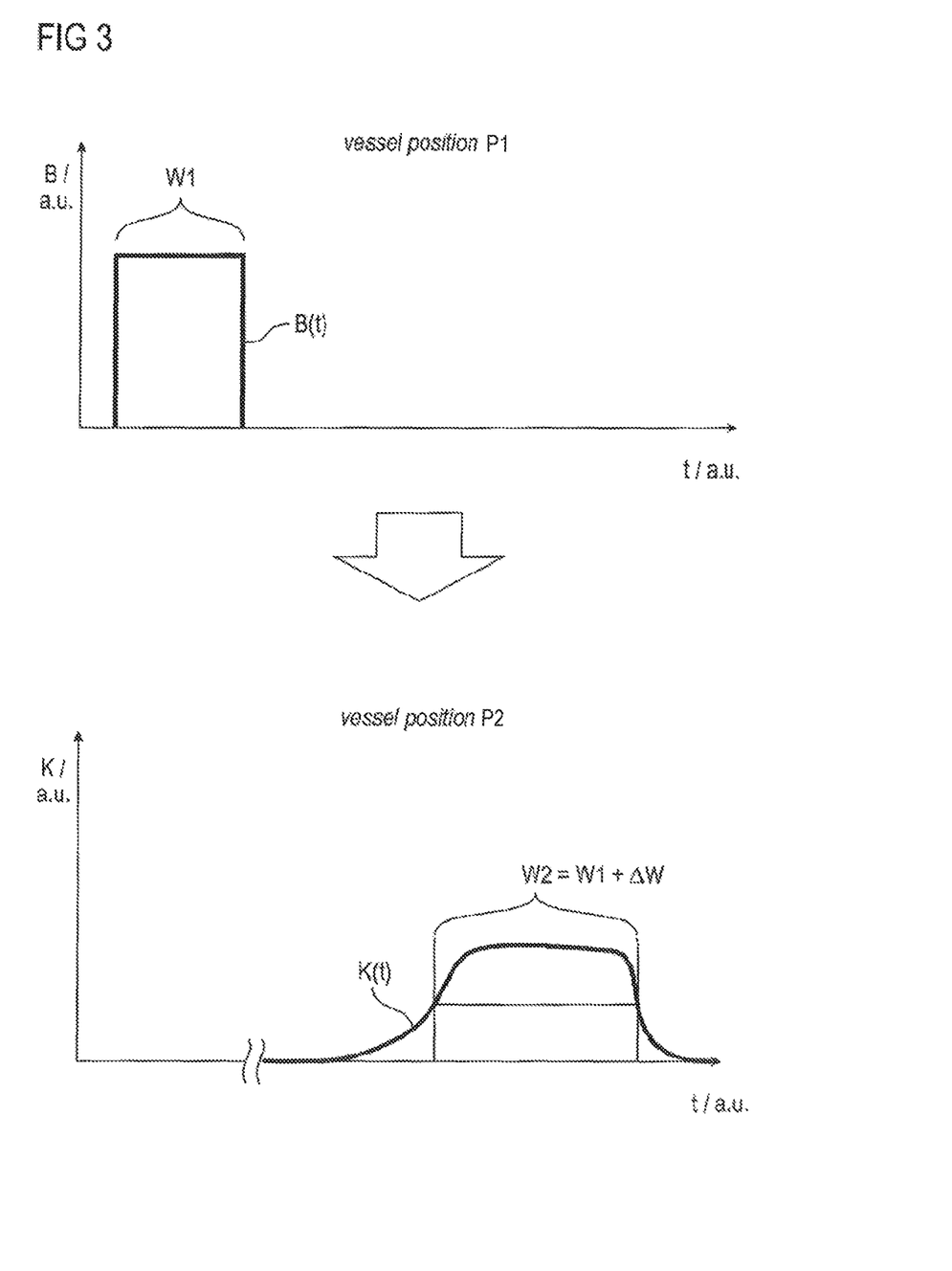
FIG. 3 shows an illustration of the change in the width of a contrast agent bolus profile at a first vessel position in relation to the width of the contrast agent concentration profile at a second vessel position.

A contrast agent bolus, which is applied at a first vessel position P1, usually has a bolus profile B(t) as plotted in the upper part of FIG. 3. There, the volume flow of a bolus B is plotted over time t. Such a bolus profile can—as depicted here—assume a rectangular profile but it can also reproduce any function B(t) by means of appropriate setting on a contrast agent injector. Such a volume flow B is selected dependent upon the employed contrast agent (e.g. Gadovist® or Magnevist®) and specific patient properties in order to achieve a desired contrast agent concentration at the location of examination in the vessel to be depicted. As shown in FIG. 2, after application in the venous vessel zone, such a bolus passes at least the heart twice and the lung with significant branching of the vessels in between. Particularly as a result thereof, but also due to additional turbulences, non-laminar flows and velocity differences across the vessel cross section, as well as thinning effects in the venous system, this creates a stronger or weaker dispersion of the applied contrast agent bolus, leading to a broadened contrast agent concentration profile K(t). At the bottom of FIG. 3, such a contrast agent concentration profile K(t) at a vessel position P2 is shown in an exemplary manner. It is easy to identify that the width of the applied bolus W1 has substantially broadened over the travelled vessel path between positions P1 and P2 such that now, taking into account a full width at half maximum, a width W2 is present. The broadening $\Delta W$ is then calculated as $\Delta W = W2 - W1$.

According to the invention, the assumption is made that the size of such broadening directly has a unique correlation with blood flow properties, measurable without a contrast agent, on the transport path of the contrast agent, or with flow parameters derivable therefrom, such that the flow-dependent broadening of an applied bolus can be determined and therefore predicted by establishing this flow parameter, in particular by using contrast agent-free measurements of blood flow properties. Then, when simultaneously establishing the bolus transfer time BTT and/or bolus arrival time BAT, it is possible to determine the time profile of the contrast agent concentration at a vessel, in particular a peripherally situated vessel, and hence predict this due to knowledge of the applied bolus. Accordingly, this naturally also allows retrospective determination of the required profile of a bolus application which leads then to a desired contrast agent concentration profile being obtained and therefore also leads to a desired signal profile in the case of an MR measurement at an ROI.

Figure 4:
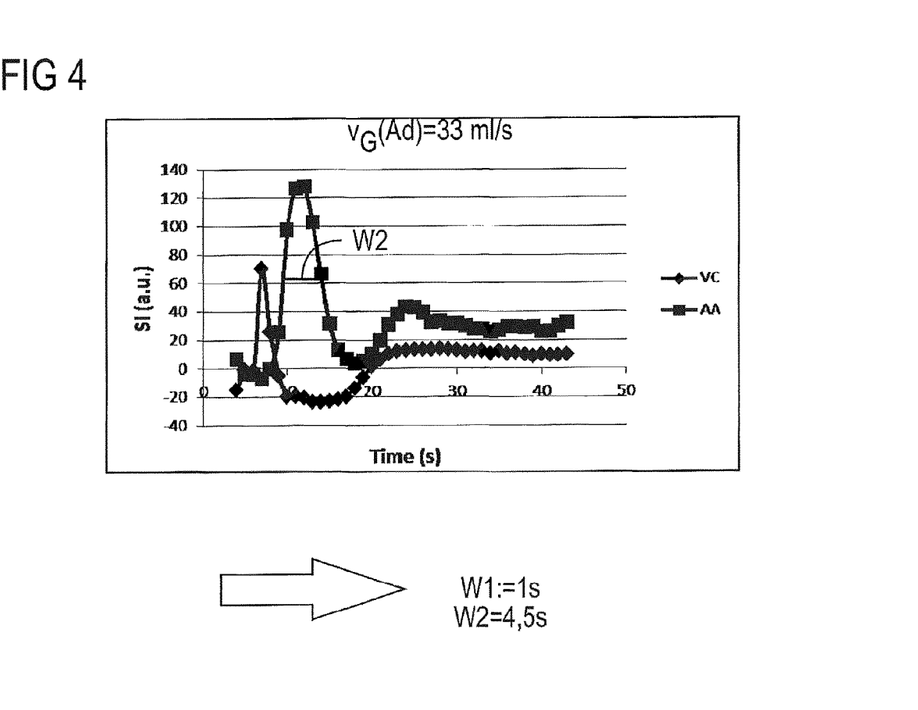
FIG. 4 shows an illustration of the measured signal strengths in a contrast agent-enhanced MR examination at the Vena cava and Aorta descendens (AD) vessel positions in the case of a laboratory animal (E639, miniature pig) in the case of a flow of 33 ml/s at the AD.
Figure 5:
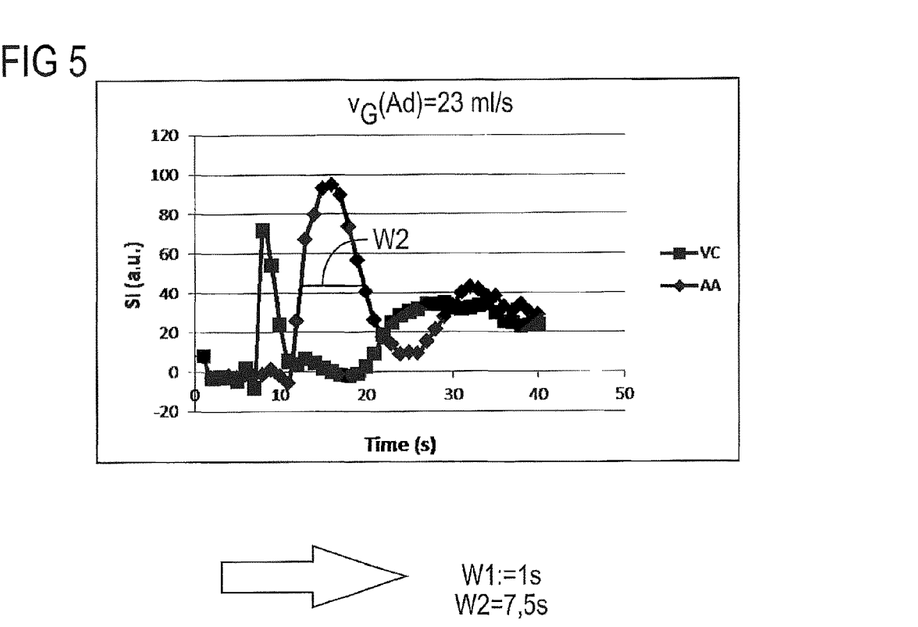
FIG. 5 shows an illustration of the measured signal strengths in a contrast agent-enhanced MR examination at the Vena cava and Aorta descendens (AD) vessel positions in the case of a laboratory animal (E639, miniature pig) in the case of a flow of 23 ml/s at the AD.

As emerges from FIGS. 4 and 5, such a correlation can be verified between a simple flow parameter—in the form of a volume flow measured without contrast agent—and the generated broadening, even in animal testing—in this case using a miniature pig.

FIG. 4 shows—corresponding to a bolus application width of W1=1 s—a measured signal profile of an MR measurement, measured directly after the application site (auricular vein) using diamond-shaped measurement points and a signal profile of an MR measurement at the Aorta descendens (AD). The mean volume flow v(AD) in the Aorta descendens, which was 33 ml/s in the shown example, was determined as the blood flow property, which is directly also used as the flow parameter. The measured width in relation to the full width at half maximum of the signal profile is 4.5 seconds. Accordingly, the broadening in relation to the bolus width W1 of 1 second was ΔW=W2−W1=4.5 s−1.0 s=3.5 s.

For comparison purposes, FIG. 5 likewise shows, with the same bolus application width of W1=1 s, a measured signal profile of an MR measurement, measured directly after the application site (auricular vein) using diamond-shaped measurement points and a signal profile of an MR measurement at the Aorta descendens (AD). However, the mean volume flow v(AD) in the Aorta descendens was 23 ml/s in this measurement. The measured width in relation to the full width at half maximum of the signal profile is 7.5 seconds. Accordingly, the broadening in relation to the bolus width W1 of 1 second was ΔW=W2−W1=7.5 s−1.0 s=6.5 s.

Thus, there clearly is a correlated relationship between the measured blood flow volume v(AD) at the Aorta descendens and the magnitude of the broadening ΔW, as was also confirmed by further experimental results.

According to the invention, such a relationship can be provided in the form of a lookup table (LUT), which is stored in a computer memory and which can serve for predetermining the broadening of a bolus.

An example of such a lookup table (LUT) for predetermining the broadening could accordingly look as follows:

TABLE 1

| W1 | $P_G^{-2}$ | $P_G^{-1}$ | $P_G^{avg}$ | $P_G^{+1}$ | $P_G^{+2}$ |
|---|---|---|---|---|---|
| $W1^{-2}$ | $\Delta W(P_G^{-2}, T1^{-2})$ | ... | $\Delta W(P_G^{avg}, T1^{-2})$ | ... | $\Delta W(P_G^{+2}, T1^{+2})$ |
| $W1^{-1}$ | ... | | ... | | ... |
| $W1^{avg}$ | $\Delta W(P_G^{-2}, T1^{avg})$ | ... | $\Delta W(P_G^{avg}, T1^{avg})$ | ... | $\Delta W(P_G^{+2}, T1^{avg})$ |
| $W1^{+1}$ | ... | | ... | | ... |
| $W1^{+2}$ | $\Delta W(P_G^{-2}, T1^{+2})$ | ... | $\Delta W(P_G^{avg}, T1^{+2})$ | ... | $\Delta W(P_G^{+2}, T1^{+2})$ |

The LUT 1 depicted in Table 1 describes the bolus broadening ΔW=W2−W1 as a function of the bolus application width W1 and of the flow parameter $P_G$. Here, using the two input parameters W1 and $P_G$, as a function of the bolus application width W1 and, in this example, a single measured parameter $P_G$, the empirically predetermined bolus broadening ΔW correlated therewith is made available. The flow parameter $P_G$ can, e.g., represent the blood volume flow, measured at the vessel position P3=Aorta descendens v(AD). The superscript indices denote the different value ranges of the parameters in the row or column headers. Intermediate values can, where necessary, be obtained by interpolation.

In a complementary or else independent manner, it is also possible in the same way to determine and represent the correlation between flow parameters measured preferably without contrast agent and the BTT or BAT. Accordingly, an appropriate LUT can be designed as follows:

TABLE 2

| BTT from P1 to P2 | $P_G^{-2}$ | $P_G^{-1}$ | $P_G^{avg}$ | $P_G^{+1}$ | $P_G^{+2}$ |
|---|---|---|---|---|---|
| $d^{-2}(ROI)/cm$ | $BTT(d^{-2}(ROI), P_G^{-2})$ | ... | $BTT(d^{-2}(ROI), P_G^{avg})$ | ... | $BTT(d^{-2}(ROI), P_G^{+2})$ |
| $d^{-1}(ROI)/cm$ | ... | | ... | | ... |
| $d^{avg}(ROI)/cm$ | $BTT(d^{avg}(ROI), P_G^{-2})$ | ... | $BTT(d^{avg}(ROI), P_G^{avg})$ | ... | $BTT(d^{avg}(ROI), P_G^{+2})$ |
| $d^{+1}(ROI)/cm$ | ... | | ... | | ... |
| $d^{+2}(ROI)/cm$ | $BTT(d^{+2}(ROI), P_G^{-2})$ | ... | $BTT(d^{+2}(ROI), P_G^{avg})$ | ... | $BTT(d^{+2}(ROI), P_G^{+2})$ |

Table 2 shows an exemplary LUT 2, in which the values for the bolus travel time $$\left(BTT = \frac{d(ROI)}{v_G(AD)} r_{fl}\right)$$

as a function of the distance d(ROI) of a selected typical vessel position from the ROI and an established flow parameter $P_G$ from measured specific blood flow properties $v_G(AP)$ and $v_G(AB)$, with $P_G=v_G(AP)/v_G(AB)$, can be read off, wherein, as a matter of principle, the BTT is derived from the flow velocity $v_G(AD)$ in the Aorta descendens, the travelled distance d(ROI) and a flow parameter-dependent correction factor $$r_{fl} = \frac{v_G(AP)}{v_G(AB)}$$

and flow velocity comes from the equation $$v_G = \frac{d}{BTT}.$$

The superscript indices in each case denote the different value ranges of the respective parameters in the row or column headers. Intermediate values can, where necessary, be obtained by interpolation.

In this LUT 2, both specific patient parameters and current flow parameters are used as input parameters for determining a bolus travel time (BTT): a patient parameter is specified in the form of a distance $d^i(ROI)$, which here constitutes the difference in cm between a vessel position P3, at which the flow parameter $r_{fl}$ is measured, and a vessel position P2 in the region of the target region ROI. Moreover, the current blood flow velocity flow parameters $v_G(AD)$, $v_G(AB)$ and $v_G(AP)$ at different vascular positions are represented as input parameters. The blood flow velocities $v_G(AP)$, representing the blood flow velocity in the region of the Aorta poplitealis in an exemplary manner, and the blood flow velocity $v_G(AB)$, representing the blood flow velocity in the region of the bifurcation in an exemplary manner, are in this case included in the LUT as quotient and correction factor and can therefore map patient-specific factors which determine the mean flow velocity and therefore the BTT. The blood flow velocity $v_G(AD)$ once again represents in an exemplary manner the blood flow velocity measured in the region of the Aorta descendens.

Therefore, the timing of a contrast agent bolus application with the contrast agent-free determination of different blood flow and patient parameters can be determined by the interaction of an accordingly adapted LUT 1 and LUT 2.

Although the invention was illustrated and described more closely in detail by the preferred exemplary embodiment, the invention is not restricted by the disclosed examples and other variations can be derived therefrom by a person skilled in the art without departing from the scope of protection of the invention. In particular, the invention is not restricted to the combination of features specified here, but it is also possible to form other combinations and partial combinations, which are clearly reproducible by a person skilled in the art, from the disclosed features. Moreover, the invention is not restricted to the claim categories used in the claims but also comprises the disclosed features in combination with all further claim categories.

Thus, overall, the invention proposes a method, in which, for the purposes of optimizing the predetermination of the time profile of a contrast agent concentration at a vessel position in a region of interest (ROI) in the case of a contrast agent-enhanced MR imaging of a patient (P) only during the first flooding-in phase of the contrast agent, the correlation of a broadening and/or a bolus transfer time of a contrast agent bolus between two vessel positions and at least one flow parameter—which constitutes a function of at least one flow property—is predetermined in the blood circulation of a patient collective such that subsequently, prior to an MR examination of a patient to be carried out, these flow parameters are determined by a contrast agent-free phase contrast MR examination and, by way of the pre-known correlations in relation to the broadening and/or bolus transfer time, the contrast agent concentration profile to be expected is determined at a vessel position in the examination region.

LIST OF REFERENCE SIGNS

1 Magnetic resonance imaging system (MRI system)
2 Magnetic coils
3 Reception coil
4 Magnetic coils
5 Contrast agent injector
6 Housing
7 Patient
8 Control and computer unit/computer with memory and display
9 Computer programs
AA Aorta ascendens
AD Aorta descendens
AP Aorta poplitealis
B Bolus
B(t) Bolus profile over time
K Contrast agent concentration
K(t) Contrast agent concentration profile over time
P1 First vessel position
P2 Second vessel position
P3 Third vessel position
P4 Fourth vessel position
ROI Examination region/region of interest
SI Signal
t Time
VC Vena cava
$v_G(AD)$ Blood flow velocity in the Aorta descendens
W1 Bolus width=bolus duration
W2 Width=duration of the contrast agent concentration profile
$\Delta W$ Broadening

The invention claimed is:

1. A method of predetermining a time profile of contrast agent concentration at a position in a blood vessel of a patient in the context of contrast agent-enhanced magnetic resonance (MR) imaging of a region of interest only during an initial flooding-in phase of the contrast agent into the blood vessel situated in the region of interest, the method comprising:
    establishing an expected broadening of a contrast agent bolus profile B(t) according to the equation $\Delta W = W2 - W1$ wherein W1 is a first width of the contrast agent bolus profile B(t) at a predetermined first vessel position of the patient and W2 is a second width of a contrast agent concentration profile K(t) at a predetermined second vessel position situated in the region of interest of the patient;
    such that the expected broadening is established by determining at least one flow parameter which is dependent on at least one blood flow property of the patient at a third vessel position thereof and which correlates with the expected broadening of the contrast agent bolus profile B(t).

2. The method according to claim 1 wherein at least one of the region of interest and the predetermined second vessel position therein is situated downstream of a cardiopulmonary passage of the patient in relation to flow of blood therein.

3. The method according to claim 2 wherein at least one of the region of interest and the predetermined second vessel position therein is situated in a peripheral region of the patient, in particular in a limb thereof.

4. The method according to claim 1 wherein the expected broadening ($\Delta W = W2 - W1$) is stored in an electronic memory for further use by a computer.

5. The method according to claim 1 wherein the at least one blood flow property is established without the presence of contrast agent by way of a phase contrast magnetic resonance measurement.

6. The method according to claim 1 wherein at least one of a bolus transfer time and a bolus arrival time is additionally determined between the predetermined first vessel position and the predetermined second vessel position.

7. The method according to claim 6 wherein the contrast agent concentration profile (K(t)) at the predetermined second vessel position is determined from the expected broadening ($\Delta W = W2 - W1$) and the at least one of the bolus transfer time and the bolus arrival time.

8. A method of predetermining a time profile of contrast agent concentration at a position in a blood vessel in a region of interest of a patient (P) in connection with a contrast agent-enhanced magnetic resonance (MR) imaging procedure to be performed on the patient, the method comprising:
    establishing a correlation between a broadening ($\Delta W = W2 - W1$) of at least one contrast agent bolus profile (B(t)) having a first width (W1) at a first vessel position (P1) in relation to a contrast agent concentration profile (K(t)) having a second width (W2) at a second vessel position (P2), the correlation being established using a flow parameter ($P_G$) dependent upon at least a blood flow property ($f_B$) of the patient (P) at a third vessel position (P3) thereof and taking into account at least one patient parameter ($P_P$) of an examined patient collective;

determining from the patient (P) at least one flow parameter ($P_{pa}$) currently representative thereof;

selecting a desired contrast agent concentration profile (K(t)) to be achieved at the second vessel position (P2) and, using the correlation, determining a necessary contrast agent bolus profile (B(t)) required therefor, taking into account at least one patient parameter ($P_P$) of the patient (P); and enabling the necessary contrast agent bolus profile (B(t)) to be one of selectable from or transmittable to an injection device for use in a contrast agent-enhanced MR examination.

9. The method according to claim 8 wherein the blood flow property ($f_B$) of the patient at the third vessel position (P3) is determined via a phase contrast magnetic resonance examination.

10. The method according to claim 9 wherein the phase contrast magnetic resonance examination for determining the blood flow property ($f_B$) is performed without the contrast agent being present in a blood circulation of the patient (P).

11. The method according to claim 8, wherein the at least one patient parameter ($P_P$): is at least one of: sex, weight, height, age, heart rate, body mass index, type of stature, and distance between the vessel positions.

12. The method according to claim 8 wherein the blood flow property ($f_B$) is at least one of:
   (a) maximum, minimum or mean blood flow velocity ($v_G$) at at least one predetermined position in a cross section of the blood vessel at the vessel position;
   (b) maximum, minimum or mean blood flow velocity ($v_G$) at at least one predetermined position in a cross section of the blood vessel at the vessel position at a given heart or pulse phase;
   (c) maximum, minimum or mean blood flow velocity ($v_G$) at at least one predetermined position in a cross section of the blood vessel at the vessel position at a given heart or pulse phase over a predetermined measurement time period;
   (d) maximum, minimum or mean blood flow volume at at least one predetermined position in a cross section of the blood vessel at the vessel position;
   (e) maximum, minimum or mean blood flow volume at at least one predetermined position in a cross section of the blood vessel at the vessel position at a given heart or pulse phase;
   (f) maximum, minimum or mean blood flow volume at at least one predetermined position in a cross section of the blood vessel at the vessel position at a given heart or pulse phase over a predetermined measurement time period;
   (g) a geometric property of a velocity profile over a cross section of the blood vessel at the vessel position; and
   (h) net forward volume over a predetermined period of time or per heartbeat.

13. The method according to claim 8 wherein the blood flow property ($f_B$) itself is used as the flow parameter ($P_G$).

14. The method according to claim 8 wherein an absolute or percentage difference between the blood flow property ($f_B$) at the third vessel position (P3) in relation to the blood flow property ($f_B$) of a same type at a fourth vessel position (P4) is used as the flow parameter ($P_G$).

15. The method according to claim 8 wherein the first vessel position (P1) satisfies at least one of the following locations or conditions:
   (a) the first vessel position (P1) lies in a venous vessel;
   (b) the first vessel position (P1) lies in an arm vein;
   (c) the first vessel position (P1) lies on the back of the hand;
   (d) the first vessel position (P1) lies at a central venous catheter;
   (e) the first vessel position (P1) lies between the back of the hand and the V. axillaris;
   (f) the first vessel position (P1) lies between a foot and the V. saphena magna; and
   (g) the first vessel position (P1) lies in a central venous vessel.

16. The method according to claim 8 wherein the second vessel position (P2) satisfies at least one of the following locations or conditions:
   (a) the second vessel position (P2) lies in an arterial vessel;
   (b) the second vessel position (P2) lies in a leg artery;
   (c) the second vessel position (P2) lies downstream of the third vessel position (P3);
   (d) the second vessel position (P2) lies downstream of the bifurcation of the aorta;
   (e) the second vessel position (P2) lies in a peripheral artery in a knee region;
   (f) the second vessel position (P2) lies in an arm region; and
   (g) the second vessel position (P2) lies in a neck region.

17. The method according to claim 8 wherein the third vessel position (P3) satisfies at least one of the following locations or conditions:
   (a) the third vessel position (P3) is the second vessel position (P2);
   (b) the third vessel position (P3) lies in the Aorta thorakalis;
   (c) the third vessel position (P3) lies in the Aorta abdominalis;
   (d) the third vessel position (P3) lies between the Aorta thorakalis and the second vessel position (P2);
   (e) the third vessel position (P3) lies upstream of the bifurcation of the aorta; and
   (f) the third vessel position (P3) lies between the bifurcation and second vessel position (P2).

18. The method according to claim 14 wherein the fourth vessel position (P4) satisfies at least one of the following locations or conditions:
   (a) the fourth vessel position (P4) lies upstream of the third vessel position (P3);
   (b) the fourth vessel position (P4) lies downstream between the third vessel position (P3) and the second vessel position (P2); and
   (c) the fourth vessel position (P4) lies downstream of the second vessel position (P2).

19. The method according to claim 8 wherein a width of the contrast agent bolus profile (B(t)) lies in the range of 3 to 15 seconds preferably but not outside of the range of 1 to 20 seconds.

20. The method according to claim 8 wherein the correlation between the broadening ($\Delta W = W2 - W1$) and the flow parameter ($P_G$) is gathered from a stored lookup table.

21. The method according to claim 20 wherein the stored lookup table is predetermined from reference measurements and the at least one patient parameter ($P_P$) is at least one of: sex, weight, height, age, heart rate, body mass index, type of stature, and distance between the vessel positions.

22. The method according to claim 8 wherein the correlation between the broadening ($\Delta W = W2 - W1$) and the flow parameter ($P_G$) is calculated by a function ($f(P_G, P_P)$) predetermined from reference measurements.

23. The method according to claim 22 wherein the at least one patient parameter ($p_p$) within the function ($f(P_G, P_P)$) is at least one of: sex, weight, height, age, heart rate, body mass index, type of stature, and distance between the vessel positions.

24. A magnetic resonance system comprising a contrast agent injector controlled by a computer, the computer being equipped with a memory for storing a program therein, the program comprising a method of predetermining a time profile of contrast agent concentration at a position in a blood vessel of a patient in the context of contrast agent-enhanced magnetic resonance imaging of a region of interest only during an initial flooding-in phase of the contrast agent into the blood vessel situated in the region of interest, the method, when executed by the computer, performing the following:
- establishing an expected broadening of a contrast agent bolus profile B(t) according to the equation $\Delta W = W2 - W1$ wherein W1 is a first width of the contrast agent bolus profile B(t) at a predetermined first vessel position of the patient and W2 is a second width of a contrast agent concentration profile K(t) at a predetermined second vessel position situated in the region of interest of the patient;
- such that the expected broadening is established by determining at least one flow parameter which is dependent on at least one blood flow property of the patient at a third vessel position thereof and which correlates with the expected broadening of the contrast agent bolus profile B(t).

* * * * *

UNITED STATES PATENT AND TRADEMARK OFFICE
CERTIFICATE OF CORRECTION

PATENT NO. : 10,852,378 B2  
APPLICATION NO. : 15/571353  
DATED : December 1, 2020  
INVENTOR(S) : Rohrer et al.

Page 1 of 1

It is certified that error appears in the above-identified patent and that said Letters Patent is hereby corrected as shown below:

In the Specification  
In Column 8, Line 28, delete "Vena axillari," and insert -- Vena axillaris, --, therefor.  
In Column 11, Line 33, delete "V. axillari;" and insert -- V. axillaris; --, therefor.  
In Column 16, Lines 62-63, delete "Aorta poplitealis" and insert -- Aorta popliteal --, therefor.  
In Column 17, Line 55, delete "Aorta poplitealis" and insert -- Aorta popliteal --, therefor.

In the Claims  
In Column 19, Line 25, in Claim 11, delete "parameter ($P_p$):" and insert -- parameter ($P_p$) --, therefor.  
In Column 21, Line 4, in Claim 23, delete "parameter ($p_p$)" and insert -- parameter ($P_p$) --, therefor.

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*